United States Patent [19]

Kramer et al.

[11] Patent Number: 4,927,806
[45] Date of Patent: * May 22, 1990

[54] SATURATED SALT/CONCENTRATED DEXTRAN FORMULATION TO TREAT HEMORRHAGE

[75] Inventors: George C. Kramer, Davis; Paul R. Perron, Citrus Heights, both of Calif.

[73] Assignee: The Regents of the University of California, Berkeley, Calif.

[*] Notice: The portion of the term of this patent subsequent to Mar. 13, 2007 has been disclaimed.

[21] Appl. No.: 41,605

[22] Filed: Apr. 23, 1987

[51] Int. Cl.$^5$ .................. A61K 37/02; A61K 31/715
[52] U.S. Cl. ............................................. 514/2; 514/54; 514/59; 514/60; 514/832; 514/833; 514/921
[58] Field of Search .................... 514/59, 60, 2, 832, 514/833, 921, 54

[56] References Cited

U.S. PATENT DOCUMENTS

| | | | |
|---|---|---|---|
| 3,864,478 | 2/1975 | Bonhard | 424/101 |
| 3,993,750 | 11/1976 | Fox, Jr. | 514/921 |
| 4,049,795 | 9/1977 | Laborit | 514/921 |
| 4,271,144 | 6/1981 | Holly | 514/59 |
| 4,308,255 | 12/1981 | Raj et al. | 424/153 |

OTHER PUBLICATIONS

Modig, cited in Biol. Abstracts 78(3) 2473 No. 21745, 1983.
Pristoupil, cited in Chem. Abstracts, vol. 82, 1975, No. 4772b.
Shimazaki, Shuji, et al. Body Fluid Changes During Hypertonic Lactated Saline Solution Therepay for Burn Shock, the Journal of Trauma, 17:38–43, 1977.
Lopes, O. U., Pontieri, V., Rocha, M., Silva, Jr., E., and Velasco, I. T., Hyperosmotic NaCl and Severe Hemorrhagic Shock: Role of the Innervated Lung, Am. J. Physiol 241 (Heart Cir. Physio 20: H883–H890) 1981.
Rush, Jr., B. F., M.D.–Treatment of Experimental Shock: Comparison of the Effects of Norepinephrine, Dibenzyline, Dextran, Whole Blood, and Balanced Saline Solutions, Surgery, vol. 61, No. 6, pp. 938–944 (1967).
Velasco, I. T., Pontieri, V., Rocha E. Silva, Jr., M., and Lopes, O. U., Hyperosmotic NaCl and Severe Hemorrhagic Shock, Am. J. Physiol. 239(5) H664–H673, 1980.
Brooks, D. K.; Williams, W. G.; Morley, R. W.; Whiteman, R., Osmolar and Electrolyte Changes in Haemorrhagic Shock, The Lancet. pp. 521–527, Mar. 9, 1963.
Silbert, Samuel, The Treatment of Thromboangiitis Obliterans, Journal A.M.A. 1759–1761 (Jun. 5, 1926).
Baue, M. D., Arthur E., et al.—A Comparison of Isotonic and Hypertonic Solutions Blood on Blood Flow and Oxygen Consumption in the Initial Treatment of Hemorrhagic Shock, J. of Trauma, vol. 7, No. 5, pp. 743–756 (1967).
Fraser, John; Cowell, E. M., Clinical Study of Blood Pressure in Wound Conditions, Journal A.M.A. Feb. 23, 1918, pp. 520-535, vol. 70, No. 8.
Danowski, T. S.; Winkler, A. W.; Elkinton, J. R.–The Treatment of Shock Due to Salt Depletion; Comparison of the Hemodynamic Effects of Isotonic Saline, of Hypertonic Saline, and of Isotonic Glucose Solutions, J.C.I. 25:130–138 (1946).
Lopes et al.; Chemical Abstracts vol. 96:617p (1982).
Velasco et al.; Chemical Abstracts vol. 93:215562r (1980).

Primary Examiner—Ronald W. Griffin
Assistant Examiner—Nancy S. Carson
Attorney, Agent, or Firm—Pretty, Schroeder Brueggemann & Clark

[57] ABSTRACT

A highly concentrated solution is provided which is both hyperosmotic and hyperoncotic with respect to blood plasma and has utility in treating patients experiencing or threatening to experience hypodynamic shock. The physiologically acceptable solution comprises a crystalloid to provide a osmolarity in excess of 5000 mOsms and a colloid to provide an oncocity in excess of 200 mm Hg. The solution is easily transported and administered by a single, rapid infusion of about less than about 1 ml/kg of body weight and results in a rapid and sustained normalization of circulatory function.

15 Claims, 1 Drawing Sheet

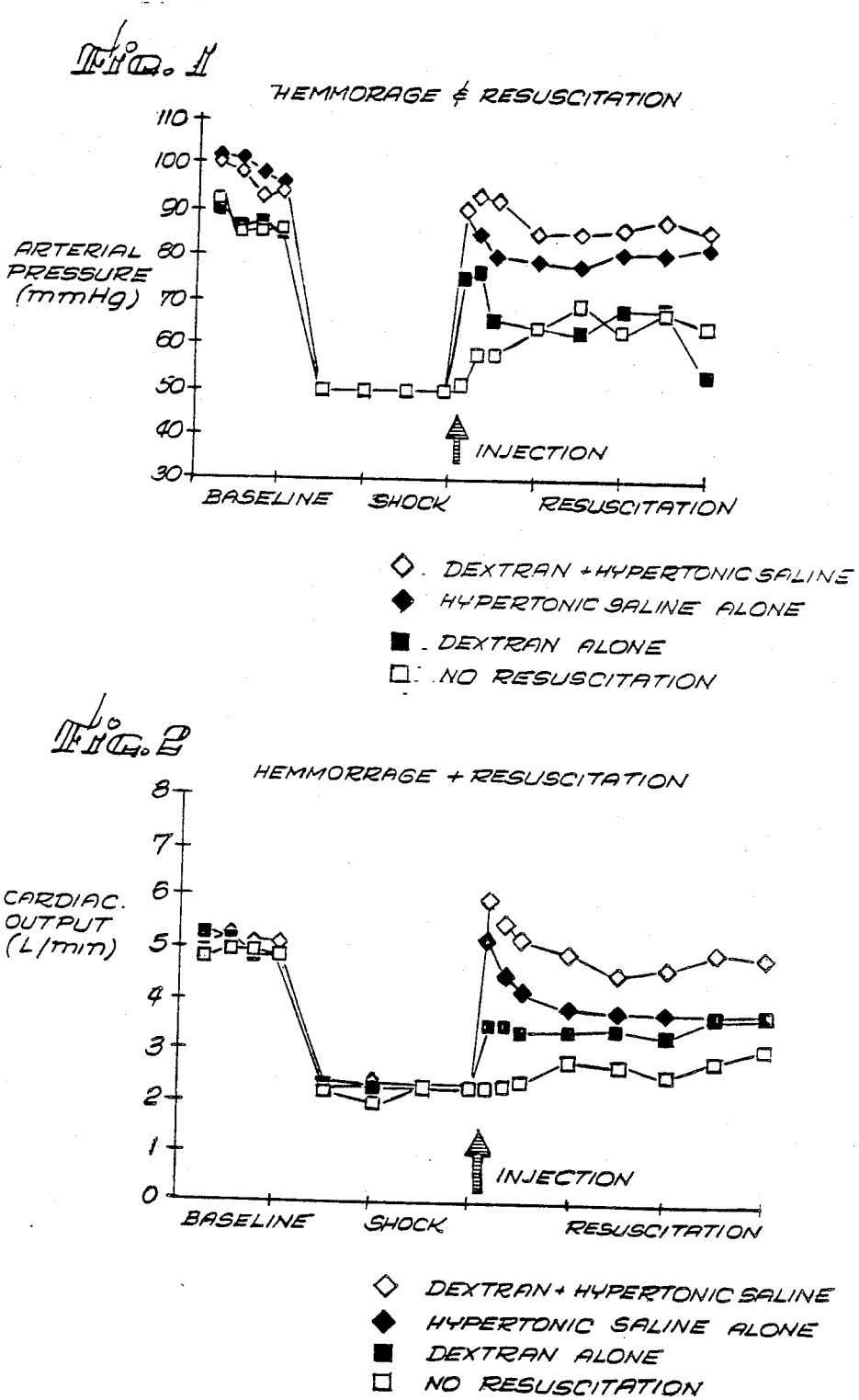

SATURATED SALT/CONCENTRATED DEXTRAN FORMULATION TO TREAT HEMORRHAGE

This invention was made with Government support under Grant No.: DAMD 17-86 C-6115 with the United States Department of Defense and the University of California. The Government has certain rights in this invention.

BACKGROUND OF THE INVENTORY

This invention relates generally to the area of treatments for circulatory shock and more specifically to a solution which is both hyperosmotic and hyperoncotic for use in preventing and treating hypodynamic shock.

Trauma is the major cause of death in persons under 38 years of age and accounts for over 150,000 deaths per year in this country. Among the most hazardous consequences of traumatic injury is bleeding. The loss of more than 50% of the starting blood volume is not unusual in such injuries and is fatal if not treated promptly.

While field therapy of many medical emergencies, such as cardiac arrest, asthmatic attacks and diabetic crisis has become increasingly successful due to the ever increasing armanentarium of effective drugs, considerably less success has been realized with field treatment of trauma and shock. No drugs have proven effective for the initial treatment of trauma victims. Initial therapy of trauma and hemorrhage currently centers on effecting the cessation of bleeding and on the infusion of large volumes of solutions to replace lost blood volume. Large volume infusion (2 to 8 liters) has generally been considered necessary to restore normal circulatory functions such as arterial blood pressure, cardiac output, oxygen consumption and renal function. Such treatment must be accomplished rapidly to be effective.

The infusion of large volumes of solution involves risks and complications, however. Fluid overload, or "overexpansion", and congestive pulmonary atelectasis may result after use of excessive amounts of fluid. Limited personnel and difficult conditions at the site of an accident make adequate field resuscitation difficult to impossible. In addition to the time necessary merely to infuse such volumes, critical minutes are lost due to difficulties in gaining access to the vascular system. Paramedical personnel must be highly trained to perform such operations. As a result, the average trauma patient has received only 700 ml of fluid prior to arrival in the emergency room, a volume which is normally insufficient to effectively treat hypodynamic shock.

Fluid replacement infusion normally utilizes solutions which have a similar osmolarity to blood plasma. Osmolarity refers to the total concentration of molecules or solutes in a solution. Water will tend to move across a semi-permeable membrane into a solution having a higher concentration of solutes. Thus, the introduction into, for example, the blood vessels, of a fluid having an osmolarity higher than that of normal body fluids will establish an osmotic gradient across the membranes, resulting in an initial change of fluid volume within the vascular system. Osmolarity is generally expresses as millimoles per liter of solution or mOsms.

Small molecules will themselves gradually leak out of the blood vessels, however, so that vascular volume will return eventually to preinfusion levels. Larger molecules, such as colloids, will not escape from the blood vessels as easily, and thus will maintain an osmotic gradient across the membranes. Because the osmotic pressure exerted by colloids in the blood, which is in the range of about 1 to 2 mOsms, is so much smaller than that of the total osmotic pressure generated by all solutes, colloidal osmotic pressure, or oncotic pressure, is expressed in terms of mm Hg. Blood plasma has an osmolarity of about 283 to 295 mOsms and an oncotic pressure of about 25 mm Hg. Solutions which exceed these levels are termed hyperosmotic or hyperoncotic, respectively.

Recently, attempts have been made to treat animals in hypodynamic shock with highly hyperosmotic saline solutions, having an osmolarity in the range of 2400 mOsms. Such treatment has the advantage of requiring smaller total fluid volume and results in brief initial promotion of circulatory function. Because this improvement is short-lived, however, with critical parameters deteriorating over time, hyperosmotic saline does not provide an effective, sustained treatment for shock.

There thus exists a longfelt need for an effective solution for treating shock victims, particularly those experiencing hypodynamic shock. Administration of a small volume of such a solution should result in the rapid and susstained normalization of circulatory function. Additionally, the solution should be inexpensive and have a long shelf life. The present invention satisfies these needs and provides related advantages as well.

SUMMARY OF THE INVENTION

The present invention provides physiologically acceptable solutions which are both hyperosmotic and hyperoncotic with respect to blood plasma and have utility in treating patients experiencing or threatening to experience hypodynamic shock. When given a small volume of the solution, on the order of 4 to 5 ml/kg of body weight, or even less if the solution is highly concentrated, patients who have lost a significant proportion of their blood volume exhibit immediate, unexpectedly improved and sustained circulatory functioning as indicated by increased arterial pressure, cardiac output, and oxygen consumption and lowered peripheral resistance. Moreover, cellular membrane potentials and intracellular electrolyte balances are thereby restored. In addition, blood flow to the kidneys and other vital organs may be augmented and urine output is unexpectedly and rapidly increased, thereby decreasing the possibility of acute renal failure, a major complication of shock. Because these solutions are effective in very small volumes, they are particularly convenient to both transport and administer.

In one embodiment, the physiologically acceptable solution comprises a hyperosmotic concentration of a crystalloid (in excess of about 1800 mOsms, preferably about 2000 to 2800 mOsms) and a hyperoncotic concentration of a colloid (in excess of about 30 mm Hg, preferably about 70 mm Hg). This solution has been found to be effective in treating victims experiencing shock when administered in a volume of 250 ml, or about 3 to 5 ml/kg. This physiologically acceptable solution is inexpensive to manufacture and is not adversely affected by temperature extremes, including freezing. As another aspect of the invention, the physiologically acceptable solution is easily administered by single, rapid infusion of approximately equal to or less than 4 to 5 ml/kg of body weight and results in a rapid and sustained normalization of circulatory function.

In another embodiment, the physiologically acceptable solution comprises a highly concentrated solution having an osmolality in excess of 5,000 mOsms, preferably about 8,000 to 15,000 mOsms, and an oncotic pressure or oncocity in excess of about 200 mm Hg, and preferably about 300 mm Hg. The maximum of concentration of the crystalloid is determined by the level at which the solution becomes fully saturated, about 29% sodium chloride in a Dextran 70 solution. The upper limit of the colloid concentration relates to the level above which the increasing viscosity of the solution makes it impractical to administer, about 30% Dextran 70.

Other features and advantages of the present invention will become apparent from the following, more detailed description which illustrates, by way of example, the principles of the invention.

BRIEF DESCRIPTION OF THE DRAWINGS

FIG. 1 shows arterial pressure as a function of time in animals receiving a hyperosmotic sodium chloride/hyperoncotic dextran solution and those receiving control solutions.

FIG. 2 shows cardiac output as a function of time in animals receiving a hyperosmotic sodium chloride/hyperoncotic dextran solution and those receiving control solutions.

DETAILED DESCRIPTION OF THE PREFERRED EMBODIMENT

The present invention provides physiologically acceptable solutions which are hyperosmotic and hyperoncotic with respect to blood plasma. The term "physiologically acceptable" as used herein means that a small volume of the solution can be injected directly into a mammal without inducing pathological changes, such as an immune response or metabolic alterations due to toxicity. The physiologically acceptable solution has particular utility for use in preventing or treating hypodynamic shock, and results in an unexpected improvement in circulatory function which is sustained for at least several hours. The solution is effective when administered in small quantities, permitting relatively easy transport and rapid administration, thereby facilitating easy and effective treatment at or near the site of injury.

The solution comprises a crystalloid and a colloid, both of which are present in concentrations exceeding those of human blood plasma, thus establishing an osmotic gradient across the walls of the blood vessels. The crystalloid may be any small molecule which will exert osmotic pressure including, but not limited to, sugars, sugar alcohols, salts, and other ions having molecular weights less than about 1000. Preferably, the crystalloid is sodium chloride, which in water comprises a saline solution. The concentration of the crystalloid is selected to provide an osmolarity which is sufficiently high so as to be effective in restoring circulatory function, without exerting detrimental effect on the cells and tissues or causing adverse physiological effects such as convulsions. Preferably, the osmolarity is between about 1800 to about 3000 mOsms, e.g., 2000 to 2800 mOsms, and ideally about 2400 mOsms. Such a solution is effective in a dose of about 4 ml/kg. Alternatively, the solution may be considerably more concentrated, having an osmolality greater than about 5,000 mOsms, preferably in the range of about 8,000 to 15,000 mOsms and ideally about 11,000 mOsms.

A colloid is also provided in the solution, selected from physiologically acceptable colloids (i.e., so-called plasma volume expanders) having an average molecular weight higher than about 30,000 and usually lower than 400,000, preferably lower than 250,000, for example lower than 100,000. Such colloids include, but are not limited to, dextran, hydroxyethyl starches and gelatins of various average molecular weights and proteins, such as plasma proteins and hemoglobin. Preferably, the colloid is dextran 70 (molecular weight of about 70,000) or dextran 60 (molecular weight of about 60,000). The concentration is selected so as to provide maximum salutory effect without damage to cells or tissues, and the colloidal osmotic pressure is higher than 30 mm Hg, preferably about 70 mm Hg which is about 6% Dextran 70, or in excess thereof. Alternatively, the solution may be of much greater concentration, having an oncocity in excess of 200 mm Hg and preferably about 300 mm Hg. Because of the problems of maximum solubility and increasing viscosity which interferes with ease of administration by the means disclosed, the concentration is preferably below about 30% weight/volume. However, concentrations of as high as about 600 mm Hg and preferably about 300 mm Hg, or 24% Dextron 70, may be usefully employed.

A hyperosmotic/hyperoncotic solution is advantageously utilized to treat hypodynamic circulatory shock resulting from such cases as hemorrhage, trauma, burns, or shock. It is also useful to treat acute renal failure and cerebral edema. The solution is administered in the field or may be used as an initial treatment in an emergency room or critical care unit where a patient exhibits rapid blood loss or unresponsive hypodynamic circulation. The solution may be infused rapidly in a single bolus through a vascular catheter or may be injected directly into a peripheral vessel, with a concomitant saving of critical time. The solution is effective in unexpectedly low dosages, which, depending on the concentratin of the solution may be equal to or less than about 4 to 5 ml/kg of body weight, or less than 1 ml/kg with a highly concentrated solution, or with a highly concentrated solution less than about 1 ml/kg body weight, which amounts to only about 10% to 0.25% the volume presently used to treat victims exhibiting shock through conventional volume replacement therapy. Because only such small volumes are necessary, logistical problems of providing the solution at the site of injury are obviated. The same volume of fluid necessary to treat one patient through conventional therapy may be effectively used to treat many patients when a hyperosmotic/hyperoncotic solution is utilized.

After administration of a small volume of a hyperosmotic/hyperoncotic solution, various indicators of circulatory function are found to rapidly achieve normality, and to sustain such normality. Among these indicators are arterial pressure, cardiac output, oxygen consumption, peripheral resistance, urine output, cellular membrane potentials and intracellular electrolyte balance.

EXAMPLE I

Comparative Treatment of Hypodynamic Circulatory Shock in Sheep

Solutions of varying composition were used to treat hypodynamic circulatory shock in adult sheep weighing 40 to 50 kg. Chronic cannultion of the thoracic aorta, superior vena cava and pulmonary artery were performed on sheep anesthetized with halothane/nitrous oxide, and silastic and Swan-Ganz thermodilution catheters (Edwards Laboratories, Santa Ana, CA) inserted. A Foley catheter was emplaced to monitor urine output. Food and water were withheld for 24 to 36 hours before the beginning of the experimental protocol. Experiments were performed at least 72 hours after surgery.

All experiments were conducted on unanesthetized animals kept unrestrained in cages. Physiological parameters measured and recorded during experiments includded vascular pressures (arterial, central venous, pulmonary artery and pulmonary wedge), cardiac output, urine flow rate, heart rate and respiratory rate. Blood samples were taken for subsequent analysis of hematocrit, serum osmolarity and serum $Na^+$, $K^+$ and $Cl^-$. After an initial one hour period of baseline data collecting, the sheep were bled to a mean arterial pressure of 50 mm Hg, and maintained at 40 to 55 mm Hg by continued bleeding for the next two hours. Measurement protocols followed those detailed in Example II.

Each experimental sheep received a bolus infusion of about 4 ml/kg of hyperosmotic/hyperoncotic solution (1.2M sodium chloride, 6% weight/volume dextran 70 (Macrodex ®, Pharmacia Fine Chemicals, Piscataway, NJ) in deionized, sterile water; osmolarity 2400 mOsms, oncotic pressure 70 mm Hg) and was monitored for three hours. Control sheep were given either no resuscitation, a hyperosmotic sodium chloride solution (1.2M, 2400 mOsms), or a hyperoncotic dextran solution (6% weight/volume, 70 mm Hg). As indicated in FIGS. 1 and 2, administration of all solutions resulted in an enhancement of cardiac output and arterial pressure. However, only the hyperosmotic/hyperoncotic solution effected a full restoration of baseline levels and resulted in sustained, near normal functioning. No other solution produced so full or sustained a response. The animals exhibited no apparent ill effect from the experimental protocol.

EXAMPLE II

Physiological Measurements

Vascular pressures were measured with a Gould P23 pressure transducer (Gould, Inc., Oxnard, CA) connected to a multichannel strip chart recorder for continuous monitoring. Transducers were leveled to the point of the shoulder. Cardiac output was measured by thermodilution, using a Model 9520A Cardiac Output Computer (Edwards Laboratories, Santa Ana, CA). Urine was collected in a closed drainage system equipped with a graduated cylinder. Hematocrits were determined with an IEC Microhematocrit Centrifuge (Damon Instruments, Needham Heights, MA). Sodium and potassium were measured by a Model 143 Flame Photometer (Instrumentation Laboratories, Lexington, MA). Blood urea nitrogen and creatinine were measured on a Clinical Chemical Analyzer System 103 (Gilford Instruments, Oberlin, OH). Osmolarity was determined on an Osmette A Freeze Point Osmometer (Precision Instruments, Sudbury, MA). Plasma volume was measured by the Evans Blue dye dilution technique (Gibson et al., J. Clin. Invest., 16:301 (1937) which is incorporated by reference).

EXAMPLE III

Comparative Efficacy of Solutions Tested

Studies were performed to compare the efficacy of a hyperosmotic/hyperoncotic solution (1.2M NaCl, 6% dextran 70), with a hyperosmotic sodium chloride solution (1.2M), a hyperoncotic dextran solution (6%) and with no resuscitative measures.

FIGS. 1 and 2 depict the effect which these solutions have on arterial pressure and cardiac output, respectively. Baseline arterial pressure ranged from about 86 to 101 mm Hg. In order to induce hypodynamic circulatory shock, the pressure was reduced to about 50 mm Hg. When no resuscitative measures were undertaken, this level rose spontaneously to about 65 mm Hg. An infusion of a small volume of dextran solution resulted in elevation of arterial pressure to about 70 mm Hg, but this level deteriorated over the course of the following three hours. An infusion of either the hyperosmotic sodium chloride solution or the hyperosmotic sodium chloride/hyperoncotic dextran solution resulted in an immediate return to baseline levels. With the hyperosmotic sodium chloride solution, however, the arterial pressure declined some 20% below baseline. The hyperosmotic sodium chloride/hyperoncotic dextran solution effects a rapid, immediate, sustained return of arterial pressure to baseline levels.

Cardiac output decreased from about 5 1/min to about 2.25 1/min upon bleeding. An infusion of a small amount of hyperoncotic dextran solution resulted in a small improvement in cardiac output while an infusion of hyperosmotic sodium chloride solution resulted in a transient return to baseline, followed by rapid deterioration. Infusion of the hyperosmotic sodium chloride/hyperoncotic dextran solution, however, not only immediately resulted in cardiac output even somewhat above baseline but a sustained level at or near baseline as well. Thus, the hyperosmotic/hyperoncotic solution results in a rapid and sustained normalization of cardiac output.

Different hyperoncotic colloid solutions were also compared. In addition to the studies referred to above utilizing hyperoncotic dextran 70, experiments were performed utilizing 1.2M sodium chloride solutions to which different colloids were added in hyperoncotic concentrations. These included hyperoncotic human albumin (25% weight/volume), hyperoncotic dextran 40 (15% weight/volume) and hyperoncotic hydroxyethyl starch (6% weight/volume). The oncotic pressure of these solutions is not known precisely, but such is well above 70 mm Hg and presumably above 150 mm Hg. Two hundred milliliters of each solution were used in an experimental protocol as in Example I. Results of the cardiac output responses are shown in Table I.

TABLE I

DIFFERENT HYPERONCOTIC SOLUTIONS EACH MIXED WITH 1.2 M SODIUM CHLORIDE IN DEIONIZED STERILE WATER
Cardiac Outout (liters/minute)

| | 25% Albumin | 15% Dextran 40 | 6% Starch |
|---|---|---|---|
| Baseline | 4.3 | 5.2 | 5.6 |
| Hemorrhage | 1.75 | 2.3 | 2.9 |
| 10 min. post resuscitation | 8.5 | 5.3 | 5.6 |
| 60 min. post resuscitation | 6.9 | 5.6 | 6.5 |
| 120 min. post resuscitation | 6.9 | 5.0 | 6.4 |

All hyperosmotic/hyperoncotic solutions resulted in an immediate and sustained improvement in cardiovascular function.

Different hyperosmotic sodium chloride solutions (1200, 1800, 2400 and 3600 mOsms) and an isoosmotic sodium chloride solution (about 285 mOsms), each mixed with 6% dextran 70 (70 mm Hg) were also compared. Results of these studies are shown in Table II. All hyperosmotic solutions were more effective than the isoosmotic solution. Cardiovascular response generally improved as osmolarity increased to 2400 mOsms. Concentrations equivalent to 3600 mOsms and higher caused convulsions. Data suggests 2400 mOsms sodium chloride/70 mm Hg dextran solution is near optimal, when given in volumes of 3-5 ml/kg.

TABLE II
SODIUM CHLORIDE SOLUTIONS OF DIFFERENT OSMOLARITIES, EACH MIXED WITH 6% DEXTRAN 70
Cardiac Outout (liters/minute)

|  | Osmolarity | | | | |
|---|---|---|---|---|---|
|  | 300 | 1200 | 1800 | 2400 | 3600 |
| Baseline | 5.1 | 5.9 | 4.9 | 5.3 | 4.3 |
| Hemorrhage | 2.2 | 2.3 | 2.1 | 2.2 | 1.8 |
| 10 min. post resuscitation | 3.2 | 4.6 | 5.0 | 6.2 | 7.0* |
| 60 min. post resuscitation | 3.1 | 4.3 | 4.8 | 4.9 | 4.8 |
| 120 min. post resuscitation | 3.2 | 4.4 | 4.3 | 4.7 | 4.3 |

*Convulsion occurred after infusion with 3600 mOsm solution.

The efficacy of a total of 6 solutions having osmolarities of about 2400 mOsms, but varying in ionic compositions and concentrations were compared using the experimental protocol in Example I. All solutions were made up in sterilized deionized water and included aqueous solutions of sodium chloride, sodium chloride/sodium acetate, sodium chloride/mannitol, sodium chloride/dextran, qlucose and sodium bicarbonate. The solutions tested are listed in Table III.

TABLE III
SIX 2400 mOsms SOLUTIONS

| NaCl | 1.2 M NaCl |
| NaHCO3 | 1.2 M NaHCO3 |
| NaAc | 0.6 M NaCl and 0.6 M NaAcetate |
| Man | 0.7 M NaCl and 1.0 M Mannitol |
| Dex | 1.2 M NaCl and 6% Dextran 70 |
| Glu | 2.4 M Glucose |

The results of the tests with these various solutions are presented in Table IV. All hyperosmotic crystalloid soltions caused a rapid improvement in cardiac output. However, the response was only sustained with the addition of a hyperoncotic colloid. With a hyperosmotic/hyperoncotic solution, such as sodium chloride (2400 mOsms)/dextran 70 (70 mm Hg), the sheep exhibited a sustained normalization of cardiac output, oxygen consumption, vascular pressures, urine output and total peripheral resistance.

TABLE IV
SIX 2400 mOsms SOLUTIONS
EFFECTS ON CARDIAC OUTPUT (liters/minute)

|  | NaCl | NaHCO3 | NaAc | Man | Dex | Glu |
|---|---|---|---|---|---|---|
| Baseline | 5.1 | 5.3 | 5.5 | 5.0 | 5.3 | 5.3 |
| Hemorrhage | 2.3 | 2.0 | 2.3 | 2.1 | 2.2 | 2.1 |
| 10 min. post resuscitation | 5.3 | 4.0 | 6.3 | 5.0 | 6.2 | 5.3 |
| 60 min. post resuscitation | 3.9 | 3.5 | 3.9 | 3.4 | 4.9 | 3.3 |
| 120 min. post resuscitation | 3.6 | 3.0 | 3.5 | 3.2 | 4.7 | 3.2 |
| 180 min. post resuscitation | 3.8 | — | 3.9 | — | 5.0 | — |

EXAMPLE IV

Survivorship of Animals Treated with Various Fluids

Experimental tests performed by Dr. Peter Maningas at the U.S. Army's Letterman Institute of Research have confirmed the efficacy of hyperosmotic/hyperoncotic solutions for treating hypodynamic shock. Experiments compared the effects of hyperosmotic and hyperoncotic solutions on survival in a severe hemorrhage rapid exsanquination model in swine (Traverso, Circulatory Shock, 12:1, (1984) which is incorporated by reference). Adult swine which were bled to 50% of estimated blood volume in 15 minutes, were treated with small resuscitation volumes of the following aqueous solutions: isoosmotic sodium chloride solution; hyperosmotic sodium chloride solution (2400 mOsms); hyperoncotic dextran solution (70 mm Hg); and hyperosmotic sodium chloride (2400 mOsms)/ hyper oncotic dextran (70 mm Hg) solution. Survival rates are shown in Table V. There was 100% survival with a solution of hyperosmotic/hyperoncotic solution while only limited success was achieved with solutions of either solute alone. No animals survived with isotonic saline or with no treatment.

TABLE V
SWINE SURVIVAL AFTER RAPID 50% BLOOD LOSS

| Resuscitation Fluid | Survival |
|---|---|
| Isoosmotic Sodium Chloride | 0 |
| Hyperosmotic Sodium Chloride | 50% |
| Hyperoncotic Dextran | 66% |
| Hyperosmotic Sodium Chloride/ Hyperoncotic Dextran Solution | 100% |

EXAMPLE V

Use of Hyperosmotic/Hyperoncotic Solution To Treat Hypodynamic Shock

A paramedic gives about 200-300 ml of a hyperosmotic/hyperoncotic solution by bolus injection into the peripheral vein of a trauma victim experiencing shock or threatening to experience shock at the scene of an accident. This small volume rapidly stabilize the patient's circulatory function until arrival at an emergency room or trauma center. This rapid restoration of cardiac output, blood pressure, renal function and oxygen consumption lowers the morbidity and mortality of trauma and hemorrhage.

Small volume resuscitation is also effective in several other hypodynamic circulatory states, such as during and after extensive surgical procedures, for burn injury and after organ transplantation, where hypodynamic shock is threatened or experienced.

EXAMPLE VI

Experimental Treatment With a Highly Concentrated Solution

Adult sheep in which hypodynamic shock was induced were treated with a small volume with a highly concentrated hyperosmotic/hyperoncotic solution. Six unanesthetized sheep weighing 36 to 43 kg were bled of more than half of their estimated blood volume (about 1500 ml) so as to maintain an arterial pressure of 50 mm Hg for 2 hours.

A solution was prepared containing 28.2% sodium chloride and 24% Dextran 70 (Macrodex, Pharmacia Fine Chemicals, Piscataway, N.J.) in deionized sterile water. The solution was calculated to have an osmolarity of about 12,000 mOsms, and an oncotic pressure (oncocity) of 24 mm Hg. The solution was almost fully saturated and had the viscosity of maple syrup. Attempts to make a more concentrated solution were abandoned because over a concentration of about 30% Dextran 70 the viscosity became too high to be acceptable for injection and was therefore unacceptable for therapeutic use.

Each experimental sheep received a bolus infusion of about 1 ml/kg body weight of this hyperosmotic/hyperoncotic solution. Physiological parameters were monitored as in Examples I and II for 3 hours post-infusion.

As indicated in Table VI, cardiac output and mean arterial pressure returned to or exceeded baseline levels shortly after administration.

TABLE VI

Resuscitation of hemorrhage with 40 ml of 28% NaCl/24% Dextran 70

|  | Mean Arterial Pressure | Cardiac Output |
| --- | --- | --- |
| Baseline | 90 ± 6 | 4.8 ± 0.3 |
| Hemorrhage | 48 ± 4 | 2.3 ± 0.8 |
| 3 min. post resuscitation | 98 ± 8 | 6.4 ± 1.6 |
| 15 min. post resuscitation | 98 ± 8 | 5.5 ± 1.3 |
| 30 min. post resuscitation | 91 ± 6 | 5.4 ± 1.4 |
| 60 min. post resuscitation | 83 ± 9 | 4.8 ± 1.3 |
| 120 min. post resuscitation | 80 ± 6 | 4.8 ± 1.4 |
| 180 min. post resuscitation | 79 ± 4 | 4.6 ± 1.2 |

Mean Arterial Pressure in mm Hg
Cardiac Output in l/minute

EXAMPLE VII

Therapeutic Treatment of Hypodynamic Shock With a Highly Concentrated Solution

A trauma victim experiencing shock, or having been injured so to be as expected to experience shock imminently, is given a bolus injection of the highly concentrated hyperoncotic/hyperosmotic solution of Example VI. The volume of solution given is sufficiently small such that it can be administered through a single syringe. The solution is preferably administered by injection into a peripheral vessel, although alternative modes of injection are possible. The amount given is about 50 ml, which is equal to about 0.7 ml/kg for a 150 pound victim. This small volume rapidly restores the cardiac output, blood pressure, renal function and oxygen consumption to near normal conditions.

Alternatively, the victim may be given multiple small doses of the solution, either by injection of about 25 ml at the time of injury followed by injection of 25 ml approximately 5 minutes later if blood pressure response to the first injection is inadequate.

Although the invention has been described with reference to the presently-preferred embodiment, it should be understood that various modifications can be made by those skilled in the art without departing from the invention. Accordingly, the invention is limited only by the following claims.

We claim:

1. A physiologically acceptable solution for treating hypodynamic circulatory shock in a mammal, said solution containing a crystalloid having a molecular weight less than about 1,000 in a concentration of at least about 5,000 mOsms and a colloid having a molecular weight in excess of 30,000 in a concentration of at least about 200 mm Hg.

2. The physiologically acceptable solution of claim 1, wherein said crystalloid concentration is between about 8,000 to 15,000 mOsms.

3. The physiologically acceptable solution of claim 1, wherein the crystalloid is selected from the group consisting of sodium salts, sugar alcohols, and sugars.

4. The physiologically acceptable solution of claim 1, wherein said colloid concentration is between about 200 to about 600 mm Hg.

5. The physiologically acceptable solution of claim 1, wherein said colloid is selected from the group consisting of dextran, hydroxyethyl starch, gelatin and protein.

6. The physiologically acceptable solution of claim 1, wherein said crystalloid concentration is about 11,000 mOsms and said colloid concentration is about 300 mm Hg.

7. A method of preventing or treating hypodynamic circulatory shock in a mammal, comprising the step of administering to said mammal in a condition of existing or impending shock, a therapeutically effective dose of a physiologically acceptable solution containing a crystalloid in a concentration of at least about 5,000 mOsms and a colloid in a concentration of at least 200 mm Hg.

8. The method of claim 7, wherein said crystalloid concentration is between about 8,000 to 15,000 mOsms.

9. The method of claim 7, wherein said crystalloid is selected from the group consisting of physiologically acceptable sodium salts, sugar alcohols, and sugars.

10. The method of claim 7, wherein said colloid concentration is between about 300 to about 600 mm Hg.

11. The method of claim 7, wherein said crystalloid concentration is about 11,000 mOsms and said colloid concentration is about 300 mm Hg.

12. The method of claim 7, wherein said colloid is selected from the group consisting of a physiologically acceptable amount of any of dextran, hydroxyethyl starch, gelatin and protein.

13. The method of claim 7, wherein said physiologically acceptable solution is infused intravascularly.

14. The method of claim 7, wherein said physiologically acceptable solution is injected.

15. The method of claim 7, wherein said therapeutically effective dose is equal to or less than 1 ml/kg of body weight.

* * * * *

UNITED STATES PATENT AND TRADEMARK OFFICE
CERTIFICATE OF CORRECTION

PATENT NO. : 4,927,806
DATED : May 22, 1990
INVENTOR(S) : Kramer et al.

It is certified that error appears in the above-identified patent and that said Letters Patent is hereby corrected as shown below:

In column 1, line 11, delete "INVENTORY" and insert therefor --INVENTION--.

In column 1, line 63, delete "expresses and insert therefor --expressed--.

In column 2, line 24, delete"susstained"and insert therefor --sustained--.

In column 4, line 21, delete "Dextron" and insert therefor --Dextran--.

In column 4, line 36, delete "concentratin" and insert therefor --concentration--.

In column 5, line 9, delete"includded" and insert therefor --included--.

In column 6, line 53, delete "Outout" and insert therefor --Output--.

In column 7, line 14, delete "Outout" and insert therefor --Output--.

In column 7, line 33, delete "qlucose" and insert therefor --glucose--.

In column 7, line 46, delete "soltions" and insert therefor --solutions--.

In column 9, line 4, after 24 insert --%--.

Signed and Sealed this

Twenty-first Day of January, 1992

*Attest:*

HARRY F. MANBECK, JR.

*Attesting Officer*       *Commissioner of Patents and Trademarks*